(12) United States Patent
Tockman et al.

(10) Patent No.: US 10,603,487 B2
(45) Date of Patent: Mar. 31, 2020

(54) IMPLANTABLE MEDICAL DEVICES AND METHODS FOR MAKING AND DELIVERING IMPLANTABLE MEDICAL DEVICES

(71) Applicant: Cardiac Pacemakers, Inc., St. Paul, MN (US)

(72) Inventors: Bruce Alan Tockman, Scandia, MN (US); Lili Liu, Maple Grove, MN (US); Brendan Early Koop, Ham Lake, MN (US); Brian Soltis, St. Paul, MN (US); Arthur J. Foster, Blaine, MN (US); G. Shantanu Reddy, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 16/119,133

(22) Filed: Aug. 31, 2018

(65) Prior Publication Data

US 2019/0001120 A1    Jan. 3, 2019

Related U.S. Application Data

(63) Continuation of application No. 14/931,628, filed on Nov. 3, 2015, now Pat. No. 10,092,745.

(60) Provisional application No. 62/074,863, filed on Nov. 4, 2014.

(51) Int. Cl.
*A61N 1/05*    (2006.01)

(52) U.S. Cl.
CPC ............. *A61N 1/059* (2013.01); *A61N 1/056* (2013.01); *A61N 1/0592* (2013.01)

(58) Field of Classification Search
CPC ....... A61N 1/059; A61N 1/056; A61N 1/0592
See application file for complete search history.

(56) References Cited

U.S. PATENT DOCUMENTS

| | | |
|---|---|---|
| 4,256,115 A | 3/1981 | Bilitch |
| 5,238,004 A | 8/1993 | Sahatjian et al. |
| 5,411,535 A | 5/1995 | Fujii et al. |
| 6,508,803 B1 | 1/2003 | Horikawa et al. |
| 7,513,903 B1 | 4/2009 | Zhao |
| 7,871,433 B2 | 1/2011 | Lattouf |
| 7,937,148 B2 | 5/2011 | Jacobson |
| 8,029,565 B2 | 10/2011 | Lattouf |
| 8,577,327 B2 | 11/2013 | Makdissi et al. |
| 8,615,310 B2 | 12/2013 | Khairkhahan et al. |
| 8,626,294 B2 | 1/2014 | Sheldon et al. |
| 8,634,919 B1 | 1/2014 | Hou et al. |

(Continued)

FOREIGN PATENT DOCUMENTS

| | | |
|---|---|---|
| WO | 2006086435 A2 | 8/2006 |
| WO | 2009135082 A1 | 11/2009 |

*Primary Examiner* — Paula J Stice
(74) *Attorney, Agent, or Firm* — Seager, Tufte & Wickhem LLP

(57) ABSTRACT

Medical devices and methods for making and using medical devices are disclosed. An example medical device may include an implantable medical device. The implantable medical device may include an implantable pacing member having a housing and a lead input. A lead may be coupled to the lead input. The lead may be designed to extend along a pericardial space, epicardium, or both and engage a heart chamber. A passageway may be defined along a portion of the length of the lead.

20 Claims, 13 Drawing Sheets

(56) References Cited

U.S. PATENT DOCUMENTS

| | | |
|---|---|---|
| 8,639,335 B2 | 1/2014 | Peichel et al. |
| 2003/0050681 A1 | 3/2003 | Pianca et al. |
| 2006/0135999 A1 | 6/2006 | Bodner et al. |
| 2007/0203554 A1 | 8/2007 | Kaplan et al. |
| 2008/0077219 A1 | 3/2008 | Williams et al. |
| 2008/0082136 A1 | 4/2008 | Gaudiani |
| 2008/0183187 A1 | 7/2008 | Bly |
| 2009/0198295 A1 | 8/2009 | Dennis et al. |
| 2013/0035748 A1 | 2/2013 | Bonner et al. |
| 2014/0128935 A1 | 5/2014 | Kumar et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2016/0067478 A1* | 3/2016 | McGeehan ......... A61N 1/0592 607/120 |
| 2017/0224995 A1 | 8/2017 | Sanghera et al. |

\* cited by examiner

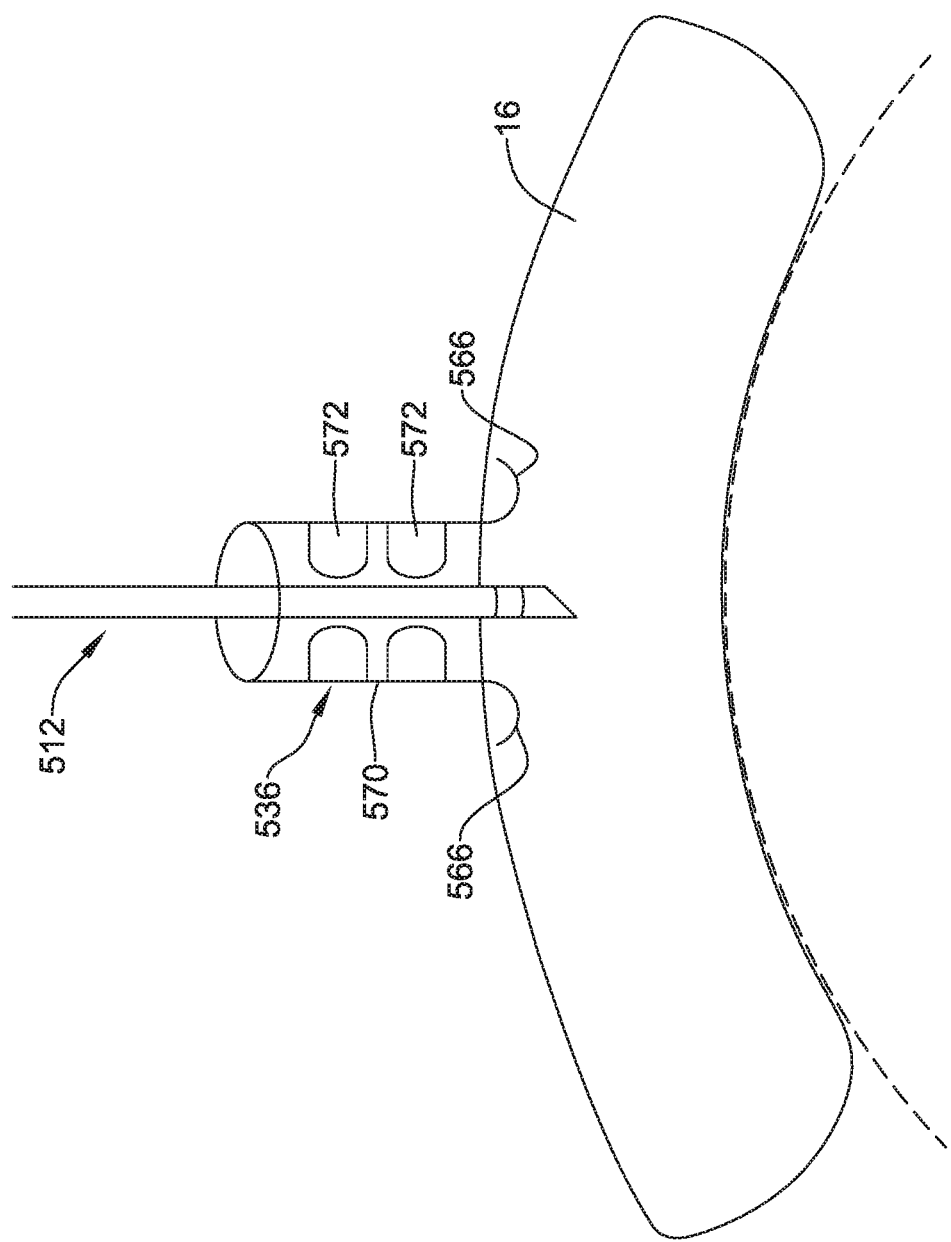

IMPLANTABLE MEDICAL DEVICES AND METHODS FOR MAKING AND DELIVERING IMPLANTABLE MEDICAL DEVICES

CROSS-REFERENCE TO RELATED APPLICATIONS

This application is a continuation of U.S. patent application Ser. No. 14/931,628, filed on Nov. 3, 2015, which claims priority under 35 U.S.C. § 119 to U.S. Provisional Application Ser. No. 62/074,863, filed on Nov. 4, 2014, the entirety of which are incorporated herein by reference.

TECHNICAL FIELD

The present disclosure pertains to medical devices, and methods for making and using medical devices. More particularly, the present disclosure pertains to implantable leads.

BACKGROUND

A wide variety of intracorporeal medical devices have been developed for medical use. Some of these devices include guidewires, catheters, implantable leads, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device may include an implantable medical device. The implantable medical device comprises:
    an implantable pacing seed having a housing and a lead input;
    a lead coupled to the lead input;
    wherein the lead is designed to extend along a pericardial space, epicardium, or both and engage a heart chamber; and
    wherein a passageway is defined along a portion of the length of the lead.
    Alternatively or additionally to any of the embodiments above, the passageway is a guidewire lumen that extends between a distal opening at a distal end of the lead and a port positioned proximal of the distal end of the lead.
    Alternatively or additionally to any of the embodiments above, the passageway extends between a closed distal end of the lead and a port positioned proximal of the closed distal end of the lead.
    Alternatively or additionally to any of the embodiments above, the lead is fixedly attached to the lead input.
    Alternatively or additionally to any of the embodiments above, the lead is detachably connected to the lead input.
    Alternatively or additionally to any of the embodiments above, a guiding member is disposed within the delivery passageway.
    Alternatively or additionally to any of the embodiments above, the guiding member is a guidewire.
    Alternatively or additionally to any of the embodiments above, the guiding member is a removable stylet.
    Alternatively or additionally to any of the embodiments above, the lead includes a pre-formed bend.
    Alternatively or additionally to any of the embodiments above, the lead includes an anchoring member designed to anchor the lead to a target location.
    An implantable medical device assembly is also disclosed. The implantable medical device comprises:
    a guidewire capable of being disposed within a pericardial space;
    a delivery catheter disposed along the guidewire, the delivery catheter having a lumen formed therein;
    a pacing lead disposed within the lumen;
    wherein the lead has a delivery passageway formed along a portion of the lead;
    an implantable pacing seed coupled to the lead, the pacing seed being designed for subcutaneous implantation; and
    an imaging device positioned adjacent to the delivery catheter.
    Alternatively or additionally to any of the embodiments above, the lead is fixedly attached to the pacing seed.
    Alternatively or additionally to any of the embodiments above, the lead is detachably connected to the pacing seed.
    Alternatively or additionally to any of the embodiments above, the delivery passageway is a guidewire lumen that extends between a distal opening at a distal end of the lead and a port positioned proximal of the distal end of the lead.
    Alternatively or additionally to any of the embodiments above, the guidewire is capable of extending through the delivery passageway.
    Alternatively or additionally to any of the embodiments above, the delivery passageway extends between a closed distal end of the lead and a port positioned proximal of the closed distal end of the lead.
    Alternatively or additionally to any of the embodiments above, a removable stylet is positioned within the delivery passageway.
    Alternatively or additionally to any of the embodiments above, the lead includes a pre-formed bend.
    Alternatively or additionally to any of the embodiments above, the lead includes an anchoring member designed to anchor the lead to a target location.
    A method for implanting a medical lead is also disclosed. The method comprises:
    positioning a guidewire within a pericardial space of a patient;
    advancing a delivery catheter along the guidewire;
    advancing a lead through the delivery catheter, the lead being coupled to a pacing seed;
    wherein a delivery passageway is defined along a portion of the length of the lead; and
    anchoring the lead to a heart chamber.
    The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

FIG. 13 illustrates an example anchoring member for anchoring an implantable lead.

Figure 1:
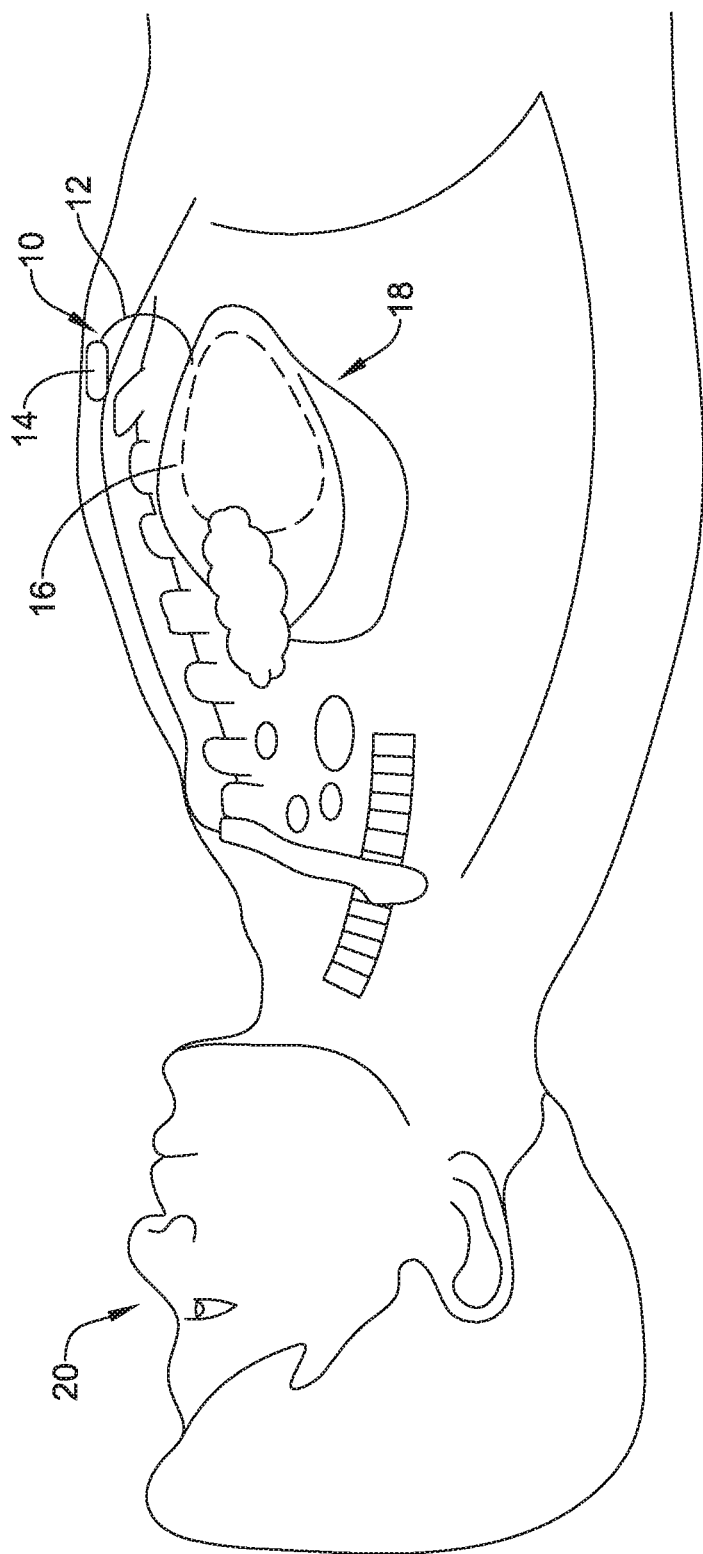
FIG. 1 is a plan view of an example medical device implanted within a patient.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A variety of pacing devices may be utilized a part of a comprehensive plan for cardiac rhythm management. Generally, these devices may include a lead that can be implanted within target tissue within the heart such as epicardial and/or myocardial tissue. The lead may be connected to an implantable pacemaker that provides a pacing signal to the lead and, ultimately, the target tissue. Placement of such leads and pacemakers may require a relatively invasive surgical procedure with a relatively high level of access to the patient's heart.

FIG. 1 illustrates an implantable medical device 10. Rather than using a relatively invasive surgical procedure, medical device 10 may be implanted using a less invasive procedure. For example, medical device 10 may be implanted by gaining access to the epicardium and/or to the pericardial space of the heart. This may include gaining access to the epicardium and/or to the pericardial space through a percutaneous sub-xiphoid approach. Once the desirable access is acquired, relatively small, low profile leads (e.g., such as a lead 12 as shown in FIG. 1) can be implanted in any of the heart chambers (e.g., right ventricle, left ventricle, right atrium, left atrium, right atrial appendage, and/or left atrial appendage), along the transvenous system, along the coronary sinus, etc. This may include the use of a catheter or suitable delivery device to facilitate implantation of lead 12. Some additional details regarding delivery of lead 12 are disclosed herein.

Figure 2:
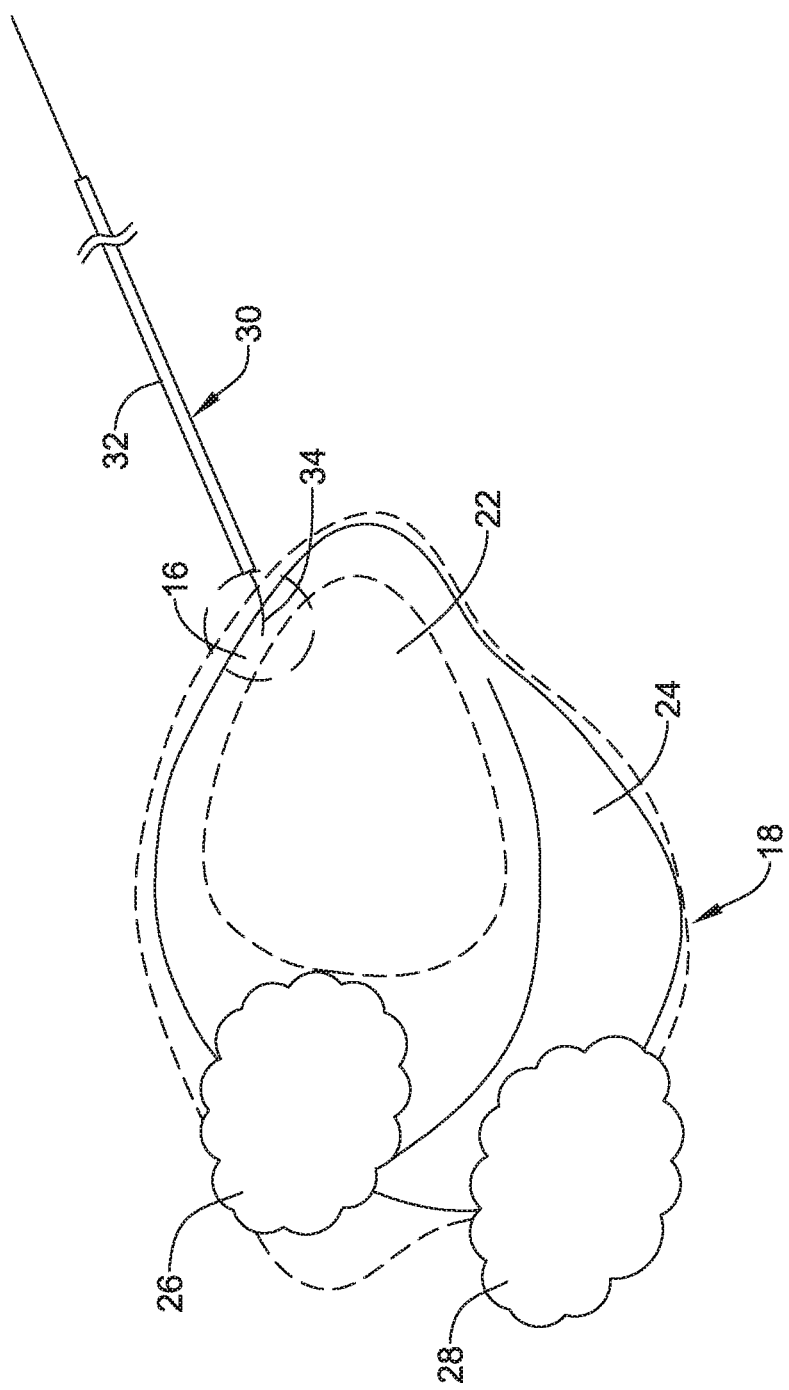
FIG. 2-5 illustrate portions of example methods for implanting an implantable medical device.

In addition to lead 12, device 10 may also include a pacing member 14 coupled to lead 12. In at least some instances, pacing member 14 takes the form of an implantable cardioverter-defibrillator, a subcutaneous implantable defibrillator, a pacing seed, or the like. Pacing member 14 is generally designed to provide electrical stimulation to cardiac tissue so as to aid in pacing, deliver cardiac resynchronization therapy, etc. The form of pacing member 14 may vary. For example, pacing member 14 may include housing or shell, a pulse generator (e.g., electrical circuitry), and a power source (e.g., a battery) within the housing to provide electrical signals to lead 12 as shown in FIG. 2. Electrical communication between pacing member 14 and lead 12 may provide electrical stimulation to heart tissue and/or sense a physiological condition. In general, pacing member 14 may be designed to be implanted subcutaneously in a patient. This may include implanting pacing member 14 percutaneously sub-xiphoid (e.g., adjacent and/or just above the xiphoid process). Placement of pacing member 14 subcutaneously may be desirable for a number of reasons. For example, such placement may allow pacing member 14 to be serviced, as needed, including replacing the generator, replacing or recharging the battery, or the like. In addition, the housing may be customized for sub-cutaneous implantation and may not require structural features that would be necessary for more invasive insertion/implantation techniques.

Pacing member 14 may include a communication module (not shown) that is designed to allow pacing member 14 to communicate with one or more additional devices. For example, pacing member 14 may include a wireless communication device that allows pacing member 14 to wireless transmit and/or receive data from a suitable module. In some of these and in other instances, pacing member 14 may be designed to communicate with another devices such as an implantable cardioverter-defibrillator, a subcutaneous implantable defibrillator, or the like, or other implantable medical devices. Wired connections are also contemplated.

In at least some instances, pacing member 14 is fixedly attached to lead 12. In other words, pacing member 14 and lead 12 are a single integrated unit. In other instances, pacing member 14 and lead 12 may be detachably connected/connectable with one another. For example, lead 12 may be detachably connected with pacing member at a lead input or plug. This may be desirable for a number of reasons. For example, should pacing member 14 need to be replaced, pacing member 14 can be detached from lead 12, removed, and a replacement pacing member 14 can be attached to lead 12. This process can be done without needing to remove or otherwise implant a new lead 12. Furthermore, should lead 12 need to be replaced, lead 12 can be detached from pacing member, removed, and a replacement lead 12 can be implanted. In some instances, a bifurcated joint may be used so that multiple leads 12 can be connected to a single pacing member 14 (e.g., by connecting the bifurcated joint to a single inline connector on pacing member 14). In addition, pacing member 14 may have a plurality of ports so that multiple leads 12 can be attached thereto.

Lead 12 may be an epicardial lead so that lead 12 may be implanted within the epicardium 16 of the heart 18 of a patient 20. However, this is not intended to be limiting. Lead 12 may also be capable of being implanted in myocardial tissue, in the ventricular walls, in the atrial wall and/or the atrial appendages, along the transvenous system, along the coronary sinus, or the like. The structure of lead 12 may also vary. In at least some embodiments, lead 12 may include one or more electrodes including bipolar electrodes, coil electrodes, sensors, and the like.

Figure 3:
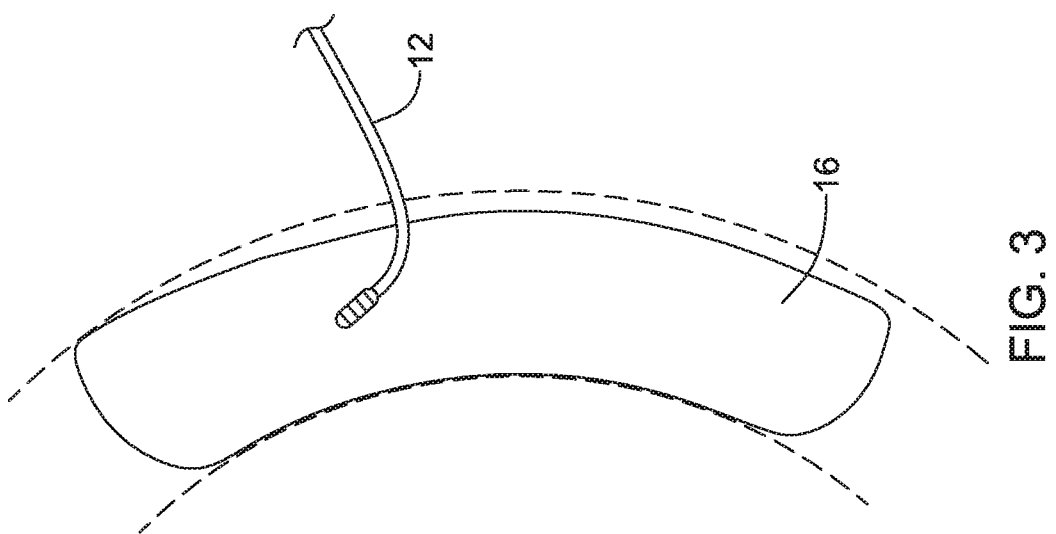
Figure 4:
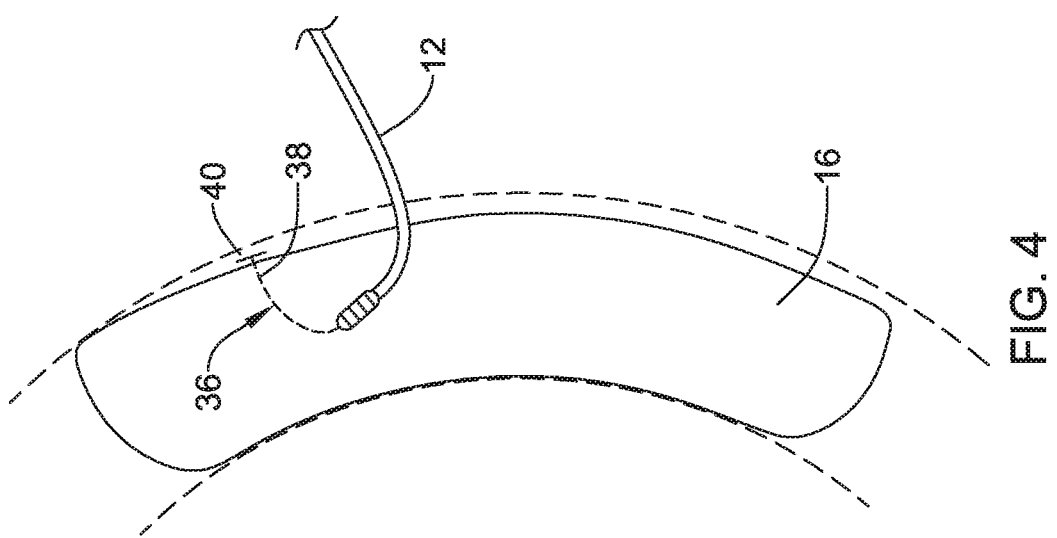

FIGS. 2-4 schematically illustrate an example method for implanting lead 12. In general, at least some of the methods contemplated may utilize a sub-xiphoid percutaneous stick in order to gain access to the pericardium and/or pericardial space so that leads (e.g., such as lead 12) can be implanted. In some instances, this may include the use of an introducer, a delivery catheter, one or more guidewires, and/or the like to advance lead 12 toward the pericardium. An imaging/visualization system (e.g., such as the SPYGLASS® direct visualization system, commercially available from Boston Scientific) may be used during the procedure to aid in guiding lead 12 to a suitable target. In some of these and in other embodiments, other visualization devices may be used including ultrasound devices (e.g., which may use echogenic feature on delivery tools, a magnetic tracking system for delivery tools, Doppler to identify blood vessels, or the like), intravascular ultrasound (IVUS), ICE® imaging devices, or the like.

The methods contemplated may allow lead 12 to be implanted in any chamber of the heart 18 including the ventricles (e.g., the left ventricle 22 or the right ventricle), the atriums, and/or the atrial appendages (e.g., the left atrial appendage 26 or the right atrial appendage 28). In the illustrations shown in FIGS. 2-4, an example method for accessing the ventricles (e.g., the left ventricle 22) is depicted. While the figures show accessing the left ventricle 22, variations to this method may also allow the right ventricle to be accessed. Modifications to access the desired location may depend on a number of factors including heart size, entry site location and angle, etc.

Delivery may utilize a delivery system 30. System 30 may include a delivery catheter or introducer 32 and a curved needle 34. After gaining pericardial access, curved needle 34 may be advanced through introducer 32 and then "stabbed" into the epicardium and/or myocardium so as to provide a track for lead 12. Lead 12 may then be implanted by advancing lead 12 along the track formed by needle 34 as shown in FIG. 3. This may include advancing lead 12 through introducer 32 (e.g., which may be a peelable introducer), through a suitable microcatheter or microintrucer, or the like.

In at least some instances, it may be desirable to utilize an anchoring mechanism to help anchor lead 12 in place along the epicardium and/or myocardium. In such case, the anchoring mechanism can be placed before, during, or after the track is formed by needle 34. For example, FIG. 4 illustrates an anchoring member 36 that may be used to anchor lead 12. In this example, anchoring member 36 includes a tether portion 38 and an anchor portion 40. Anchor portion 40 has a T-shaped end that can provide a surface to grip the surface of the tissue and substantially prevent migration of anchoring member 36. In use, lead 12 may be advanced along tether portion 38 to a suitable location (e.g., which may be right behind anchor portion 40 when a unipolar/monopolar lead 12 is used or for a bipolar lead 12 both electrodes could be closely spaced within the myocardial wall or the proximal electrode could reside on the epicardial surface). When suitably positioned, tether portion 38 could be tied in a knot or otherwise secured so that the position of lead 12 is substantially fixed relative to anchoring member 36. While the "T-bar" type of anchoring member 36 is illustrated, other anchoring members are contemplated including intrinsic anchoring members secured directly to lead 12 (e.g., a helix, tines, a clip, hooks, barbs, etc.), anchoring members placed before or after placing lead 12, shape memory anchoring members that may be held in a more straightened or altered configuration (e.g., within needle 34) and then allowed to take an altered shape within the target tissue sufficient to anchor, or the like. In some instances, the anchoring mechanism may include structures formed from a bioabsorbable material. Accordingly, the anchoring mechanism may be relied upon for initially anchoring lead 12 but then the anchoring mechanisms degrades or absorbs over time. Therefore, after a suitable amount of time, tissue growth around lead 12 may be sufficient to maintain lead 12 in place even in the absence of the "initial" anchoring mechanism.

In some instances, lead 12 (and/or other leads disclosed herein) may include a pre-formed bend. The pre-formed bend may aid in the delivery of lead 12, for example. The pre-formed bend may be positioned near the distal end of the lead 12 or along other suitable locations.

Figure 5:
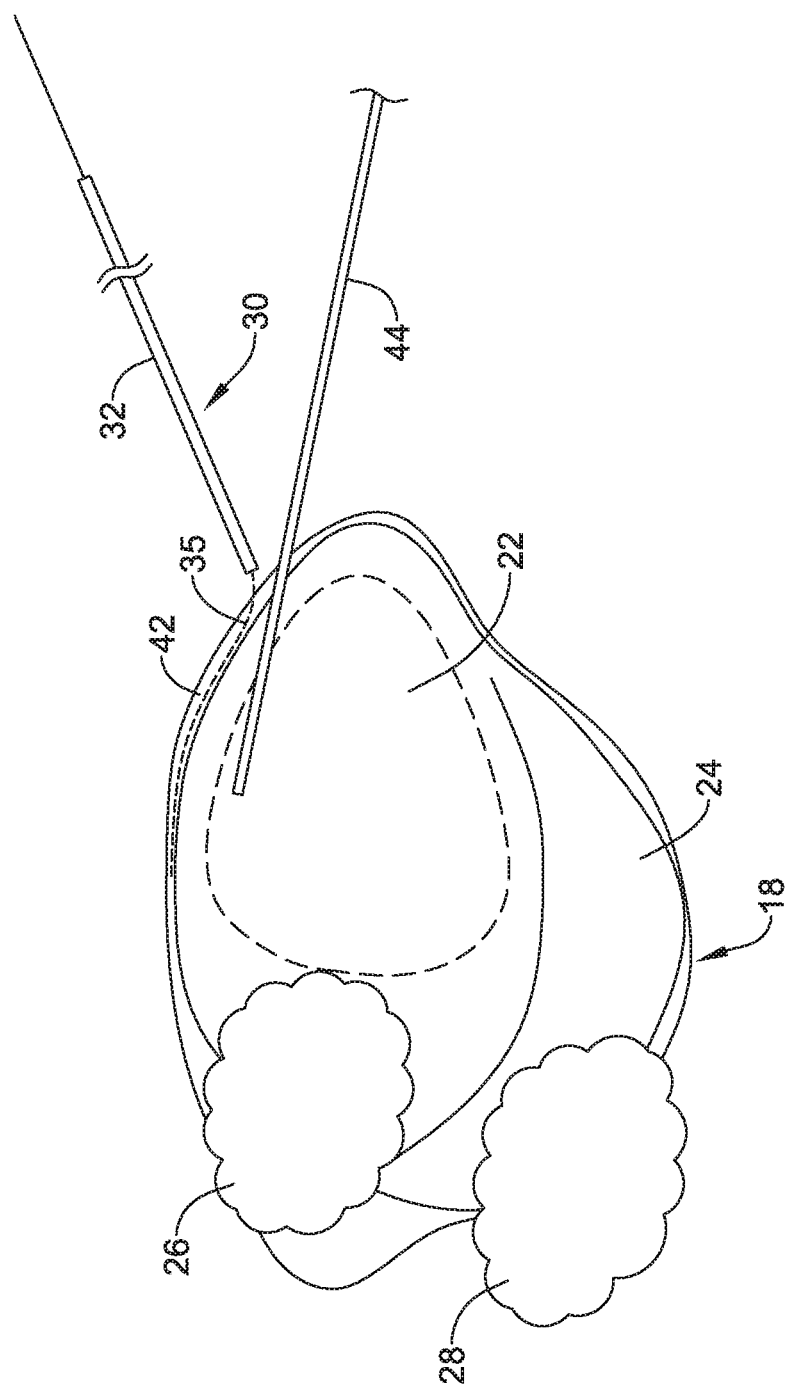

For atrial lead placement, the methods for implanting lead 12 may be modified. For example, FIG. 5 schematically illustrates that after gaining pericardial access (e.g., using a needle to stab into the pericardium and/or a curved needle to make a curved pathway into the pericardium), delivery system 30 may be used to place a guidewire 35 within the pericardial space 42. Guidewire 35 may be tracked through pericardial space 42 to either the right or left atrial appendage. If desired, a relatively small catheter (not shown) can be tracked over guidewire 35 to provide a conduit for lead 12. An imaging system 44 (SPYGLASS®, ultrasound, Doppler, IVUS, or the like) may be used along with system 30 in order to aid in guiding of lead 12 to a suitable target. Lead 12 may be advanced along guidewire 35 to a target tissue. Upon reaching the target, lead 12 may be anchored using a suitable anchoring mechanism. The anchoring mechanism may be similar to anchoring member 36, may take the form of a helix or the like secure to lead 12, etc. When securing lead 12, the anchoring mechanism may bring the electrode(s) of lead 12 into suitable contact with the target tissue (e.g., which may be the outer surface of the atrial appendage or may be within cardiac tissue).

With lead 12 placed at the desired target location, a variety of pacing strategies may be employed. For example, pacing may occur at any heart chamber or combination of heart chambers (e.g., left atrium and left ventricle, right atrium and right ventricle, etc.). Biventricular (BiV) pacing may also be utilized.

Figure 6:
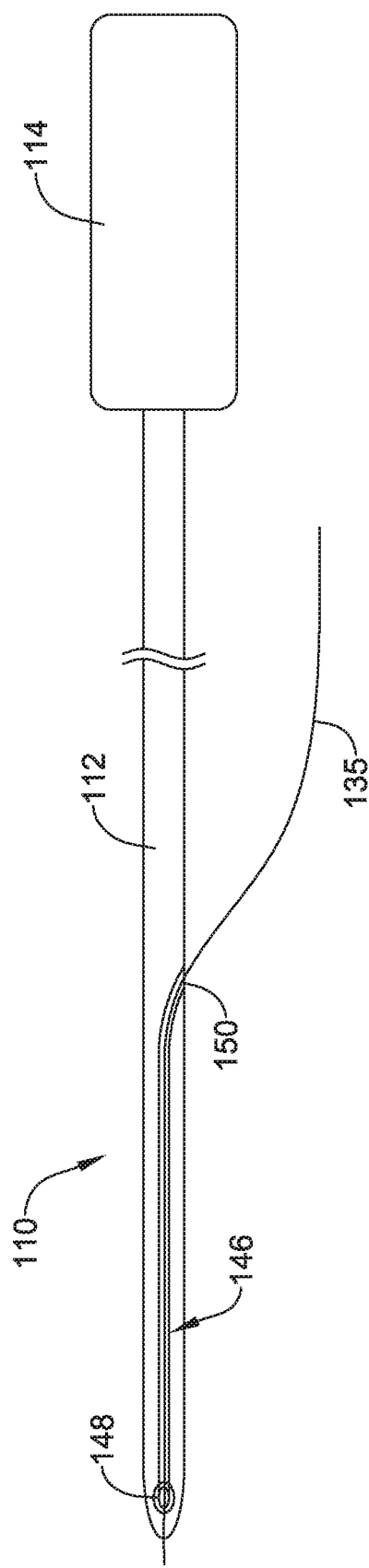
FIG. 6 is a side view of an example implantable medical device.

FIG. 6 schematically illustrates implantable medical device 110, which may be similar in form and function to other medical devices disclosed herein and which may be implanted as disclosed herein. Device 110 may include lead 112 and pacing member 114. In this example, lead 112 and pacing member 114 as shown as a single, integrated structure where lead 112 is directly wired with pacing member 114. In other words, lead 112 is fixedly attached to pacing member 114. However, other embodiments are contemplated where lead 112 is detachably connected to pacing member 114.

As shown, lead 112 may have a lumen or passageway 146 defined at least a portion of the length thereof. Passageway 146 extends between a distal end port 148 and a proximal port 150. Proximal port 150 is positioned proximally of distal end port 148 a relatively short distance so that passageway is akin to a "rapid exchange" or "single operator exchange" lumen of a catheter. Accordingly, passageway 146 may be used to track lead 112 over guidewire 135 and/or an anchoring mechanism during implantation of lead 112.

Figure 7:
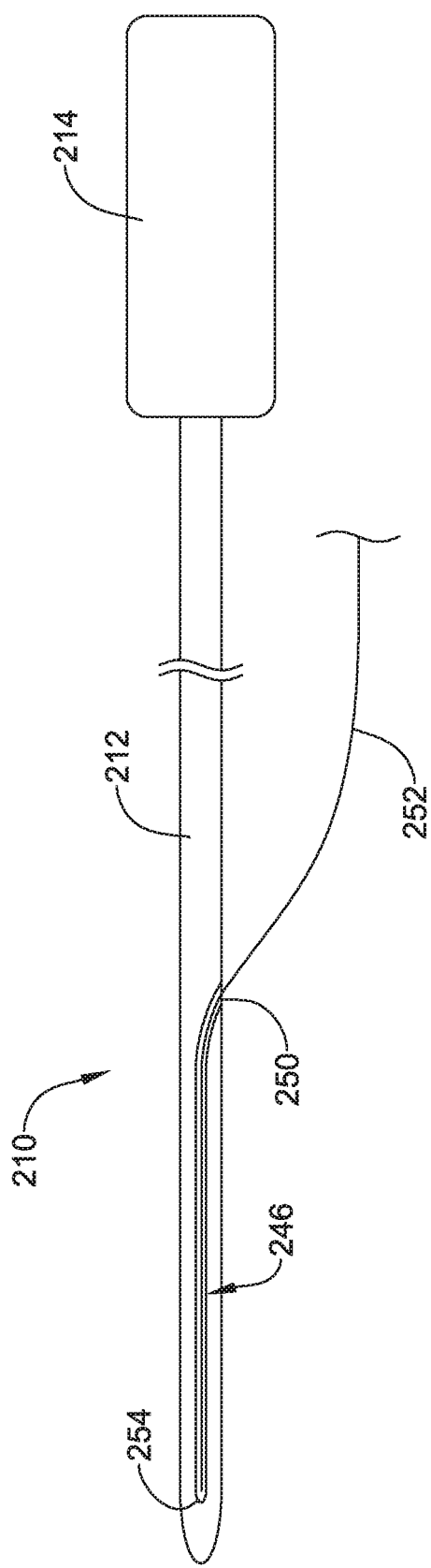
FIG. 7 is a side view of an example implantable medical device.

FIG. 7 illustrates implantable medical device 210, which may be similar in form and function to other medical devices disclosed herein. Device 210 may include lead 212 and pacing member 214. In this example, passageway 246 takes the form of a closed end passageway 246 that is defined between a closed distal end 254 and proximal port 250. Passageway 246 may be used in conjunction with a removable stylet 252. Stylet 252 can be inserted into passageway 246 and pushed distally to advance lead 212 into position. In addition, stylet 252 may be rotated in order to effect rotation of lead 212. In at least some embodiments, stylet 252 may include steering features so that actuation of the steering mechanism may bend or curve stylet 252 (and, thus, lead 212) into a curved configuration. This may aid in guiding lead 212 to the desired target location. In some of these and in other embodiments, stylet 252 may have one or more pre-formed bends (e.g., an "S" curve, sine wave shape, etc.). This may provide strain relief.

Figure 8:
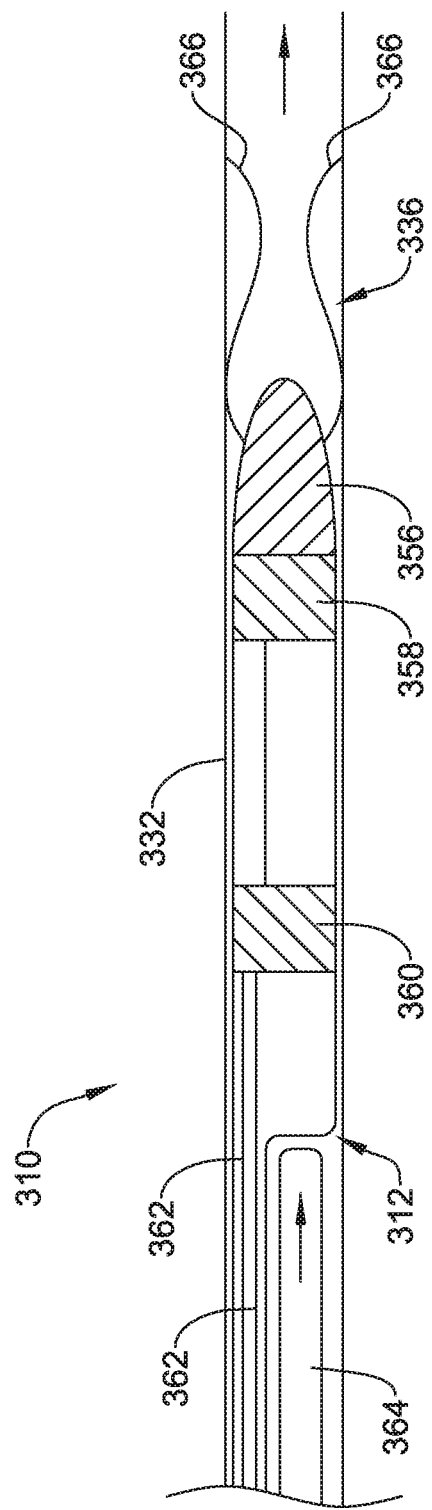
FIGS. 8-11 illustrate an example method for implanting an implantable medical device.

FIG. 8 illustrates implantable medical device 310, which may be similar in form and function to other medical devices disclosed herein. Device 310 may include lead 312. Lead 312 may be disposed within delivery sheath or catheter 332. At the proximal end, lead 312 may be attached to a pacing member (not shown) similar to those disclosed herein. Lead 312 may include a tip member 356, a cathode 358, an anode 360, and connector wire or members 362. These structural features are just examples. Other forms and structures are contemplated.

In at least some instances, lead 312 may include a passageway such as passageway 146/246 on lead 112/212. Accordingly, lead 312 may be advanced along a guidewire and/or may be pushed or guided with a stylet. In other instances, lead 312 has a body without a lumen or passageway. However, lead 312 may be oriented so that connector wires 362 are offset from the central axis of lead 312. This allows for a push member 364 to be disposed within catheter 332. Push member 364 may be utilized to push lead 312 distally from catheter 332 during delivery of lead 312.

Figure 9:
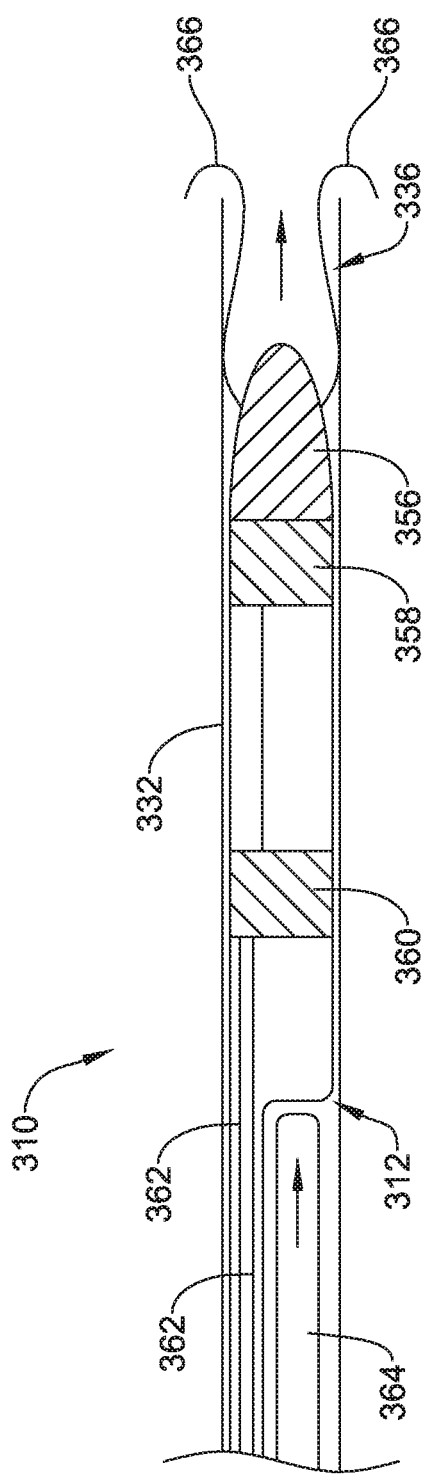
Figure 10:
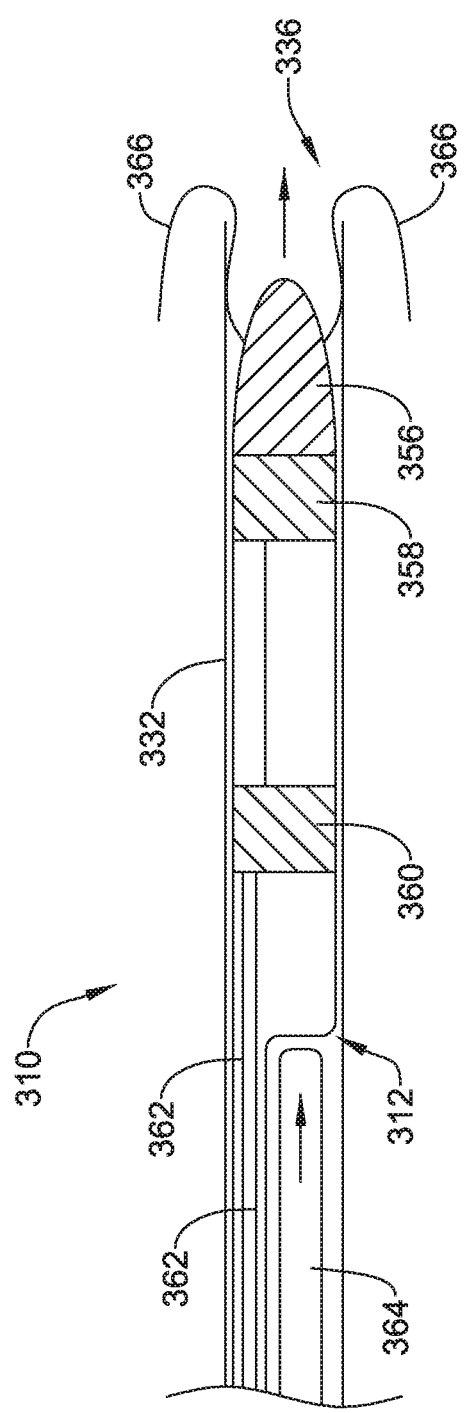
Figure 11:
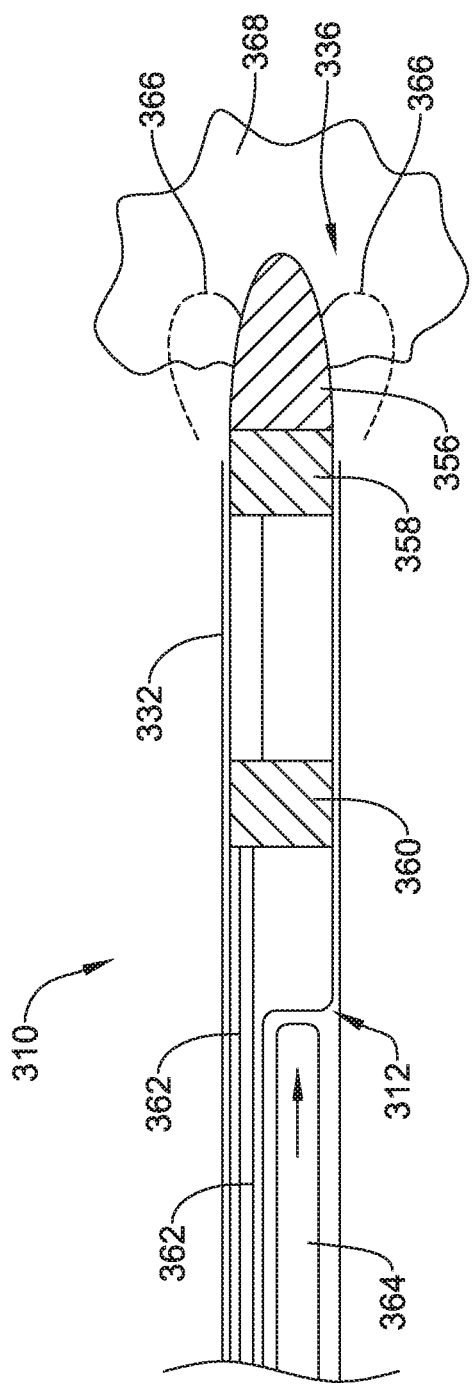

Lead 312 may also include anchor member 336. In this example, anchor member 336 may include a pair of tines 366. Tines 366 may take the form of metallic hooks with one or more preformed bends. In some examples, tines 366 may be formed from a nickel titanium alloy. Other materials are contemplated including those disclosed herein. During delivery, tines 366 may be positioned so that they extend distally from tip member 356 within catheter 332. Push member 364 may be used to advance lead 312 within catheter 332. When doing so, tines 366 may begin to emerge from catheter 332 as shown in FIG. 9. The preformed bends in tines 366 may begin to shift tines 366 proximally. If the position of lead 312 is not satisfactory, lead 312 may be proximally retracted within catheter 332 and repositioned. If the position is deemed satisfactory, lead 312 may be advanced further as shown in FIG. 10. Again, if the position of lead 312 is not satisfactory, lead 312 may be proximally retracted within catheter 332 and repositioned. If the position is deemed satisfactory, lead 312 can be further advanced until tines 366 are completely out from catheter 332 and so that tines 366 may engage with target tissue 368 as shown in FIG. 11.

Figure 12:
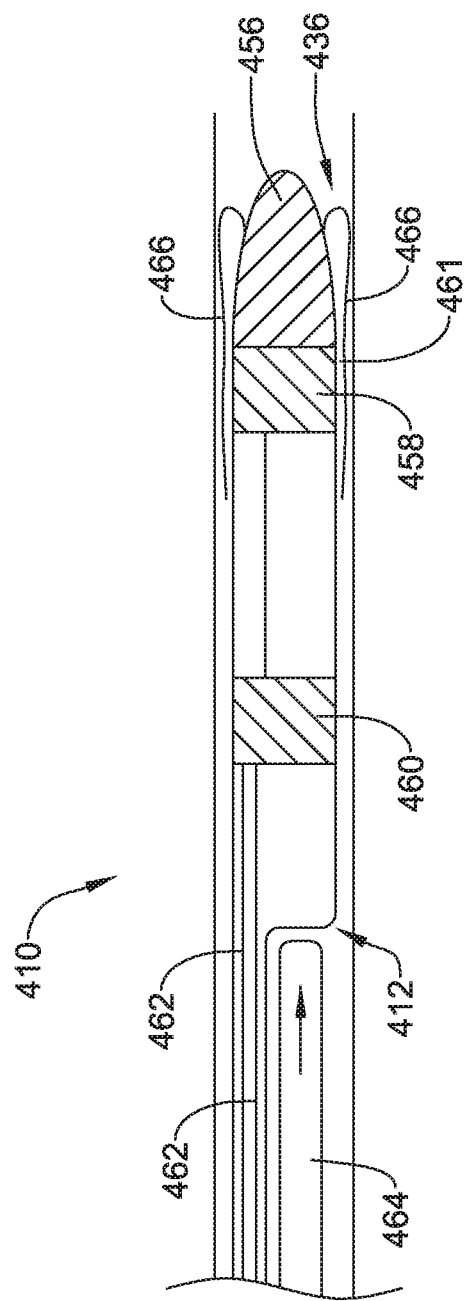
FIG. 12 illustrates a portion of an example implantable medical device.

While tines 366 extending distally within catheter 332 are one possible anchoring mechanism that may be used with lead 312, this is not intended to be limiting. Other anchoring mechanisms are contemplated that vary in shape, structure, form, etc. For example, FIG. 12 illustrates implantable medical device 410, which may be similar in form and function to other medical devices disclosed herein. Device 410 may include lead 412 and catheter 432. Lead 412 may include tip member 456, cathode 458, anode 460, and connector wires 462. Push member 464 may be disposed within catheter 432. Lead 412 may also include anchor member 436. In this example, anchor member 436 may include a pair of tines 466 oriented proximally within catheter 432. In use, push member 464 may be used in a manner similar to push member 364 to advance lead 412 out from catheter 432.

A number of additional anchoring mechanisms are also contemplated. For example, anchoring members that are intended to dig into or other penetrate target tissue (e.g., epicardium, myocardium, etc.) may be utilized. In addition, other structures may be disposed along the lead that may function by stabilizing the position of the lead. For example, an expandable stent-like structure may be positioned adjacent to the distal end of the lead that is designed to expand within and stabilize the position of the lead. Other structures such as expandable balloons, baskets, struts, and the like are also contemplated.

FIG. 13 illustrates anchoring member 536 that may be used to secure lead 512 (and/or other leads disclosed herein) within epicardium 16. In this example, anchoring member 536 may include a tubular body 570. Tines 566 may be coupled to body 570. Tines 566 may be designed to engage target tissue (e.g., epicardium 16, myocardium, etc.) and secure tubular body 570 in place. Anchoring member 536 may also include engagement members 572 disposed within body 570 for engaging lead 512. In this instance, engagement members 572 are projections disposed along the interior of tubular body 570 that are capable of frictionally engaging and securing lead 512.

The materials that can be used for the various components of device 10 (and/or other devices disclosed herein) may include those commonly associated with medical devices. For simplicity purposes, the following discussion makes reference to device 10. However, this is not intended to limit the devices and methods described herein.

Device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of device 10 to achieve the same result.

In some embodiments, a degree of Magnetic Resonance Imaging (MRI) compatibility is imparted into device 10. For example, device 10 or portions thereof, may be made of a material that does not substantially distort the image and create substantial artifacts (e.g., gaps in the image). Certain ferromagnetic materials, for example, may not be suitable because they may create artifacts in an MRI image. Device 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

U.S. patent application Ser. No. 14/451,586, filed Aug. 5, 2014, is herein incorporated by reference.

U.S. patent application Ser. No. 14/451,601, filed Aug. 5, 2014, is herein incorporated by reference.

U.S. patent application Ser. No. 14/451,564, filed Aug. 5, 2014, is herein incorporated by reference.

U.S. patent application Ser. No. 14/451,553, filed Aug. 5, 2014, is herein incorporated by reference.

U.S. patent application Ser. No. 14/452,654, filed Aug. 6, 2014, is herein incorporated by reference.

U.S. patent application Ser. No. 14/452,617, filed Aug. 6, 2014, is herein incorporated by reference.

U.S. patent application Ser. No. 14/452,680, filed Aug. 6, 2014, is herein incorporated by reference.

U.S. patent application Ser. No. 14/452,607, filed Aug. 6, 2014, is herein incorporated by reference.

U.S. patent application Ser. No. 14/452,641, filed Aug. 6, 2014, is herein incorporated by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method of implanting an implantable medical device within a patient, comprising:
    implanting a lead interior of the patient's rib cage by advancing the lead along an arcuate path, the lead including at least one electrode; and
    subcutaneously implanting a pacing member exterior of the patient's rib cage, the pacing member including a housing, a pulse generator within the housing, and a power source within the housing;
    wherein a proximal end of the lead is connected to a lead input of the pacing member exterior of the patient's rib cage and a distal end of the lead is located interior of the patient's rib cage.

2. The method of claim 1, wherein the lead is detachably connected with the pacing member at the lead input.

3. The method of claim 1, wherein the at least one electrode comprises at least two electrodes including bipolar electrodes.

4. The method of claim 1, wherein the lead is positioned in contact with an epicardium of the patient's heart.

5. The method of claim 1, wherein the lead is positioned in a pericardial space of the patient.

6. The method of claim 1, wherein the lead includes a guidewire lumen extending therein.

7. The method of claim 6, wherein the step of implanting the lead includes advancing the lead along a guidewire disposed in the guidewire lumen.

8. The method of claim 1, further comprising anchoring a distal end of the lead within the patient.

9. A method of implanting an implantable medical device within a patient, comprising:
    implanting a lead between the patient's rib cage and the patient's heart by advancing the lead along an arcuate path, the lead including at least one electrode; and
    subcutaneously implanting a pacing member exterior of the patient's rib cage, the pacing member including a housing, a pulse generator within the housing, a power source within the housing, and a lead input;
    wherein a proximal end of the lead is detachably connected to the lead input of the pacing member exterior of the patient's rib cage and a distal end of the lead is located interior of the patient's rib cage.

10. The method of claim 9, wherein the step of implanting the lead includes advancing the lead along an arcuate path.

11. The method of claim 9, wherein the at least one electrode comprises at least two electrodes including bipolar electrodes.

12. The method of claim 9, further comprising:
    positioning the lead in contact with an epicardium of the patient's heart.

13. The method of claim 9, further comprising:
    positioning the lead in a pericardial space of the patient.

14. The method of claim 9, further comprising:
    anchoring a distal end of the lead within the patient.

15. The method of claim 9, wherein the lead includes a guidewire lumen extending therein.

16. The method of claim 15, wherein the step of implanting the lead includes advancing the lead along a guidewire disposed in the guidewire lumen.

17. The method of claim 9, wherein the lead includes a pre-formed bend.

18. A method of implanting an implantable medical device within a patient, comprising:
    implanting a distal end of a lead interior of the patient's rib cage, the lead including at least one electrode; and
    subcutaneously implanting a pacing member exterior of the patient's rib cage, the pacing member including a housing, a pulse generator within the housing, and a power source within the housing;
    wherein a proximal end of the lead is connected to the pacing member;
    wherein the lead includes a pre-formed bend.

19. The method of claim 18, wherein the at least one electrode comprises at least two electrodes including bipolar electrodes.

20. The method of claim 18, wherein the proximal end of the lead is detachably connected to a lead input of the pacing member.

* * * * *